United States Patent [19]

Lellouche et al.

[11] Patent Number: 5,519,128
[45] Date of Patent: May 21, 1996

[54] PROCESS FOR THE SYNTHESIS OF ACYLATED DERIVATIVES OF FATTY ACID-TRANSPORTING THIOLS AND IN PARTICULAR ACYL-COENZYMES A AND THE THUS OBTAINED ACYL-COENZYMES A

[75] Inventors: Jean-Paul Lellouche, Les Ulis; Karine Levannier, Rueil-Malmaison; Charles Mioskowski, Strasbourg, all of France

[73] Assignee: Commissariat a l'Energie Atomique, Paris, France

[21] Appl. No.: 392,172

[22] Filed: Feb. 22, 1995

Related U.S. Application Data

[62] Division of Ser. No. 210,300, Mar. 18, 1994, Pat. No. 5,424,415.

[30] Foreign Application Priority Data

Mar. 31, 1993 [FR] France .................................. 93 03744

[51] Int. Cl.⁶ .................................................. C07H 17/00
[52] U.S. Cl. ......................................................... 536/26.23
[58] Field of Search ............................................ 536/26.23

[56] References Cited

U.S. PATENT DOCUMENTS 5,424,415 6/1995 Lellouche et al. .................... 536/26.23

*Primary Examiner*—Herbert J. Lilling
*Attorney, Agent, or Firm*—Oblon, Spivak, McClelland, Maier & Neustadt

[57] ABSTRACT

The invention relates to a process for the synthesis of an acylated derivative of a fatty acid-transporting thiol such as the coenzyme A.

According to this process, a silylated or stannylated thiol is prepared by reacting the thiol with a silylation or stannylation reagent in order to at least partly replace the unstable hydrogens of the thiol by $SiR_3$ or $SnR_3$ groups with R being an alkyl or aryl group. The silylated or stannylated thiol is then reacted in an anhydrous organic medium with an activated organic acid and a deprotection reagent able to eliminate the silyl or stannyl groups.

In this way it is possible to obtain acylated derivatives of the coenzyme A, in which the acyl group can have up to 30 carbon atoms with high yields.

3 Claims, No Drawings

PROCESS FOR THE SYNTHESIS OF ACYLATED DERIVATIVES OF FATTY ACID-TRANSPORTING THIOLS AND IN PARTICULAR ACYL-COENZYMES A AND THE THUS OBTAINED ACYL-COENZYMES A

This is a division of application Ser. No. 08/210,300 filed on Mar. 18, 1994 now U.S. Pat. No. 5,424,415.

The present invention relates to a process for the synthesis of acylated derivatives of fatty acid-transporting thiols and in particular acyl-coenzymes A.

Acyl-coenzymes A are very interesting derivatives usable in numerous biosynthetic procedures, particularly for the study of biological mechanisms involving fatty acids.

Several methods for preparing acyl-coenzymes A are known. Most of these methods use the condensation reaction of an acid activated with the coenzyme A, at ambient temperature, in the aqueous phase or in an organic solvent—water medium. The activated acid can be a mixed anhydride, a chloride or an ester of N-hydroxysuccinimide or an acyl imidazole, as is described by E. R. Staddtman, Methods in Enzymol. 1957, vol.3, 931–941; Peter Goldman and P. Roy Vagelos, J. Biol. Chem. 1961, 236, 2620–2623; Frank Davidoff and Edward D. Korn, J. Biol. Chem. 1964, 239, 2496–2506; Adhid Al-Arif and Melvin Blecher, J. Lipid Res. 1969, 10, 344–345; Adhid Al-Arif and Melvin Blecher, Biochim. Biophys. Acta. 1971, 248, 416–429; Maynard E. Pullman, Anal. Biochem. 1973, 54, 188–198; James E. Bishop and Amiya K. Hajra, Anal. Biochem. 1980, 106, 344–350; and Akihiko Kawaguchi, Tsutomu Yoshimura and Shigenobu Okuda, J. Biochem. 1981, 89, 337–339.

These methods are difficult to perform, because they are based on the reaction of a highly hydrophilic compound (coenzyme A), which is soluble in water, but insoluble in most organic solvents, with an organic acid, which is often insoluble in water. Therefore, in order to perform the condensation reaction, it is necessary to mix an aqueous solution in which is dissolved the coenzyme A with an organic solvent containing the activated acid and check the pH throughout the reaction, which gives rise to performance difficulties. Moreover, this method cannot be used when the activated acid has a very long hydrocarbon chain, e.g. more than 18 carbon atoms. Finally, the yields obtained by these methods are not reproducible due to the reaction performance difficulties.

The present invention specifically relates to a process for the synthesis of acylated derivatives of fatty acid-transporting thiols, which obviates these disadvantages and which is also applicable to the preparation of acylated derivatives in which the acyl radical has more than 18 carbon atoms.

According to the invention, the process for the synthesis of an acylated derivative of a fatty acid-transporting thiol by reacting the thiol with an acylation reagent comprises the following stages:

1°) preparing a silylated or stannylated thiol by reacting, in an organic solvent, the thiol with a silylation or stannylation reagent in order to at least partly replace the unstable hydrogens of the thiol by groups of formula $SiR_3$ or $SnR_3$, in which the R's, which can be the same or different, are alkyl or aryl groups and 2°) reacting the silylated or stannylated thiol in an anhydrous organic solvent with a) a deprotection reagent in order to eliminate the $SiR_3$ or $SnR_3$ groups and with b) the acylation reagent in order to obtain the acylated derivative of the thiol.

In this process, due to the preparation in the first stage of a silylated or stannylated thiol, it is possible to solubilize the fatty acid-transporting thiol, which generally has a highly hydrophilic character in an anhydrous organic solvent and then facilitate the condensation reaction of the thiol with the acylation reagent.

Therefore it is then possible to perform this condensation reaction in an anhydrous organic medium without having to check the pH, which makes it possible to obtain high acylated derivative yields in a reproducible manner.

The fatty acid-transporting files used in the process of the invention are more or less complex organic molecules having a SH group by which they can be associated with various fatty acids.

As examples of such molecules reference can be made to coenzyme A, which is a complex molecule having numerous unstable hydrogens, cysteamine, which is a much simpler molecule of formula $NH_2$—$C_2H_4$—$SH$, carnitine and pantothenic acid.

Coenzyme A has the following formula:

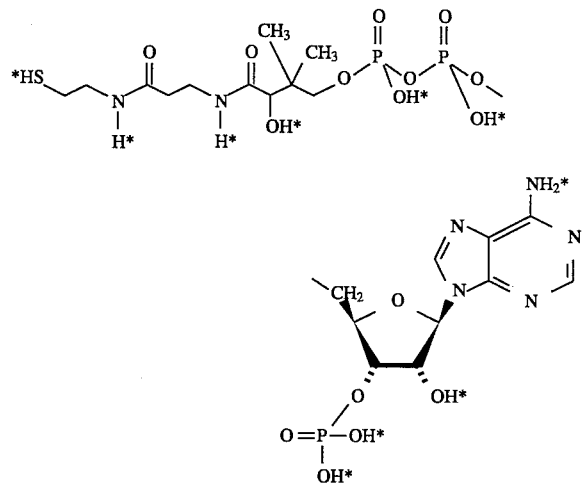

On the basis of this formula, it can be seen that it is possible to protect the 11 functions (hydroxyl, amide, amine, phosphate and thiol) indicated hereinbefore by asterisks, by silyl or stannyl groups.

The replacement of unstable hydrogens by such groups in this very polar, hydrophilic compound reduces said polarity and therefore reduces the possibilities of hydrogen bonds forming and therefore in general terms favours the solubility of the compound in both polar and non-polar, organic solvents.

The process according to the invention is also of particular interest for preparing acylated derivatives of coenzyme A.

In the first stage of the process according to the invention, preparation consequently takes place of a silyated or stannylated thiol by reacting, in an organic solvent, the starting thiol with a silylation or stannylation reagent in order to at least partly replace the unstable hydrogens of the thiol by groups of formulas $SiR_3$ or $SnR_3$ in which the R's, which can be the same or different, are alkyl or aryl groups.

The alkyl groups can be straight or branched and generally have 1 to 6 and preferably 1 to 4 carbon atoms. The aryl groups generally have 6 to 15 carbon atoms.

As an example of such aryl groups, reference can be made to phenyl and naphthyl. Preferably, in the first stage, the thiol is reacted with a silylation reagent.

Various silylation reagents can be used, but particular preference is given to 1-methoxy-2-methyl-1-trimethylsiloxypropene, because by reacting the thiol with this reagent as the byproduct of the reaction are obtained very volatile compounds, namely isopropyl acetate and hexamethyldisiloxane respectively having boiling points of 85° and 101° C., which can therefore be easily eliminated from the reaction medium by evaporation.

Moreover, when the thiol is coenzyme A, the use of this silylation reagent has the advantage of silylating the thiol functions in a neutral medium, which avoids the dimerization of the coenzyme A.

The silylation reaction can be performed directly on the thiol or by placing it in solution in an organic solvent such as acetonitrile or dichloromethane and adding to the solution the silylation agent, which is allowed to react at ambient temperature for the desired time. At the end of the reaction elimination takes place of the solvent, if necessary, the silylation byproducts and the excess reagent by evaporation under reduced pressure.

In the case of coenzyme A, the silylation reaction can lead to a protection of the 11 previously indicated functions. However, under the reaction conditions used, it is not certain that all these functions are silylated, but in general 7 functions are silylated, including the thiol function.

In the case where a stannylation reaction is performed, it is possible to use as the stannylation reagent, an identical reagent and operate under similar conditions.

Following silylation or stannylation, the condensation reaction of the thiol is performed on the acylation reagent in an anhydrous, organic medium also using a deprotection reagent for eliminating the $SiR_3$ or $SnR_3$ groups on the thiol functions, which must react with the acylation reagent.

In order to carry out this deprotection, it is possible to use as the reagent a fluoride or other reagents able to eliminate the $SiR_3$ or $SnR_3$ groups.

As examples of such deprotection reagents, reference can be made to tetrabutyl ammonium fluoride, tetrabutyl ammonium difluorotriphenyl stannate, aluminium trichloride, potassium fluoride, cesium fluoride and rubidium fluoride.

In preferred manner, according to the invention, the deprotection reagent is cesium fluoride or rubidium fluoride. Thus, the other fluorides give less satisfactory results and this also applies to the other reagents mentioned hereinbefore.

When using cesium fluoride and rubidium fluoride it is also possible to speed up the reaction either by subjecting the reaction medium to a sonication, or by operating in the presence of a catalyst constituted by a crown ether such as dicyclohexyl-18-C-6 (DCH-18-C-6) of formula:

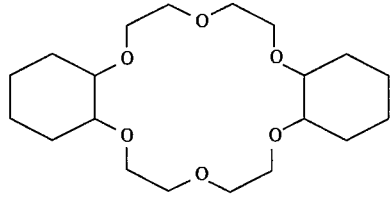

or tris-(3,6-dioxaheptyl)-amine (TDA-1) of formula:

$N(CH_2CH_2OCH_2CH_2OCH_2)_3$.

The use of TDA-1 is advantageous, because it is not toxic.

For carrying out the condensation, it is possible to use as the acylation reagent the saturated or unsaturated, activated acids generally used for this purpose such as mixed anhydrides, acid chlorides, thioesters and esters.

These activated acids can be substituted by various substituents such as OH, F, the cyclopropyl group, etc. Examples of activated acids of this type are described in Journal of American Chemical Society, vol. 114, 1992, pp.2245–2251; vol. 113, 1991, pp.7388–7397 and vol.115, 1993, pp.1619–1628.

Preferably, according to the invention, the acylation reagent used is an ester or a mixed anhydride of an optionally substituted, saturated or unsaturated carboxylic acid. The ester can in particular be an ester of a carboxylic acid or N-hydroxysuccinimide, N-hydroxyphthalimide or 2,4,6-trichlorobenzyl alcohol.

Examples of usable carboxylic acids are octadecanoic acid, icosanoic acid, arachidonic acid, oleic acid, linoleic acid, linolenic acid, 3-hydroxyicosanoic acid, 3-oxoicosanoic acid, 2-icosenoic acid, (2-heptadecyl-1,3-dioxolan-2-yl)-acetic acid, 2-fluoro-2-icosenoic acid and 4-fluoro-3-hydroxyicosanoic acid.

The organic solvents used in this second stage for performing the desilylation or destannylation and condensation reaction can be chosen from among polar or non-polar organic solvents such as tetrahydrofuran (THF), dichloromethane, hexane, acetonitrile, acetone, dimethyl ether, ethyl acetate, alcohol, diethyl ether, etc.

Preferably, according to the invention, the organic solvent used is dimethyl ether, tetrahydrofuran, acetonitrile or mixtures thereof.

In the second stage a choice is made of the quantities of acylation reagent and thiol in such a way as to optimize the acylated derivative yield. Good results are obtained when the molar ratio of the acylation reagent to the thiol is 1:1 to 2:1.

This second stage can be performed at ambient temperature or at a temperature below or above this, e.g. at temperatures of 0° to 25° C. for periods between 1 and 10 hours.

The temperature and duration of the condensation reaction are in particular dependent on the deprotection reagent used. Thus, when using as the reagent cesium fluoride in the presence of DCH-18-C-6, preference is given to working at a temperature of 25° C. for 3 to 5 hours. However, when the deprotection reagent used is cesium fluoride subjecting the reaction medium to a sonication, preference is given to working at 0° C. for approximately 90 minutes.

The invention also relates to the silylated or stannylated coenzyme A obtained in the first stage of the process. This silylated coenzyme A complies with the following formula:

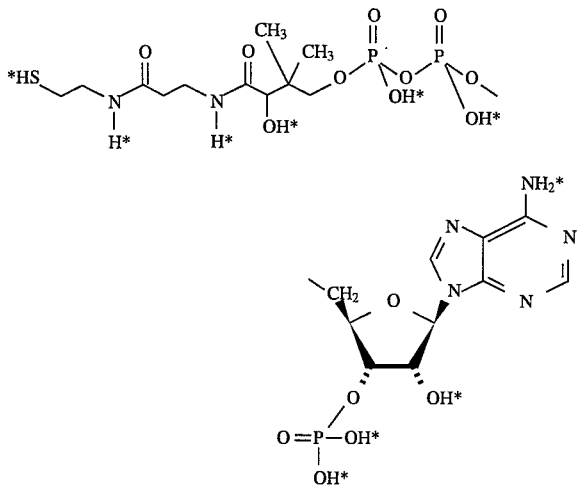

in which at least part of the unstable hydrogens H* are replaced by a group of formula $SiR_3$, in which the R's, which can be the same or different, are alkyl groups and in particular $C_1$ to $C_4$ alkyl groups or aryl groups.

The invention also relates to the acyl-coenzymes A obtained by this process, in which the acyl group complies with the formula $R^1CO—$, in which $R^1$ is a hydrocarbon group with 20 to 29 carbon atoms and 0 to 6 double bonds.

Other features and advantages of the invention can be better gathered from reading the following examples given in an illustrative and non-limitative manner.

These examples illustrate the preparation of acylated derivatives of the coenzyme A (CoASH) obtained by reacting the silylated coenzyme A (silylated CoASH) with an activated acid (icosanoic acid or octadecanoic acid of formula $R^1—COOH$ with $R^1$ representing $CH_3(CH_2)_{16}$ or $CH_3(CH_2)_{18}$) in accordance with the process of the invention.

This preparation corresponds to the following reaction diagram relating to examples 1 and 2.

containing 10 mg (13.0 µmole) of coenzyme A trihydrate (SIGMA) dissolved in 0.5 ml of freshly distilled acetonitrile. Stirring takes place at 25° C. under nitrogen and it is found that the medium becomes homogeneous after 40 min reaction. After 12 h reaction, evaporation takes place of the solvent, the silylation byproducts and the reagent excess under reduced pressure in order to obtain a colourless oil constituted by the silylated derivative of coenzyme A.

2) Preparation of the acylated derivative of coenzyme A.

a) Preparation of the ester of icosanoic acid and N-hydroxysuccinimide.

To 3.0 mmole of icosanoic acid in solution in 10 ml of anhydrous ethyl acetate are added 340 mg (3.0 mmole) of N-hydroxysuccinimide (ALDRICH) in solution in 3 ml of anhydrous ethyl acetate, followed by the addition of 610 mg (3.0 mmole) of dicyclohexyl carbodiimide (ALDRICH) in solution in 3 ml of anhydrous ethyl acetate. The reaction mixture is maintained under nitrogen at ambient temperature

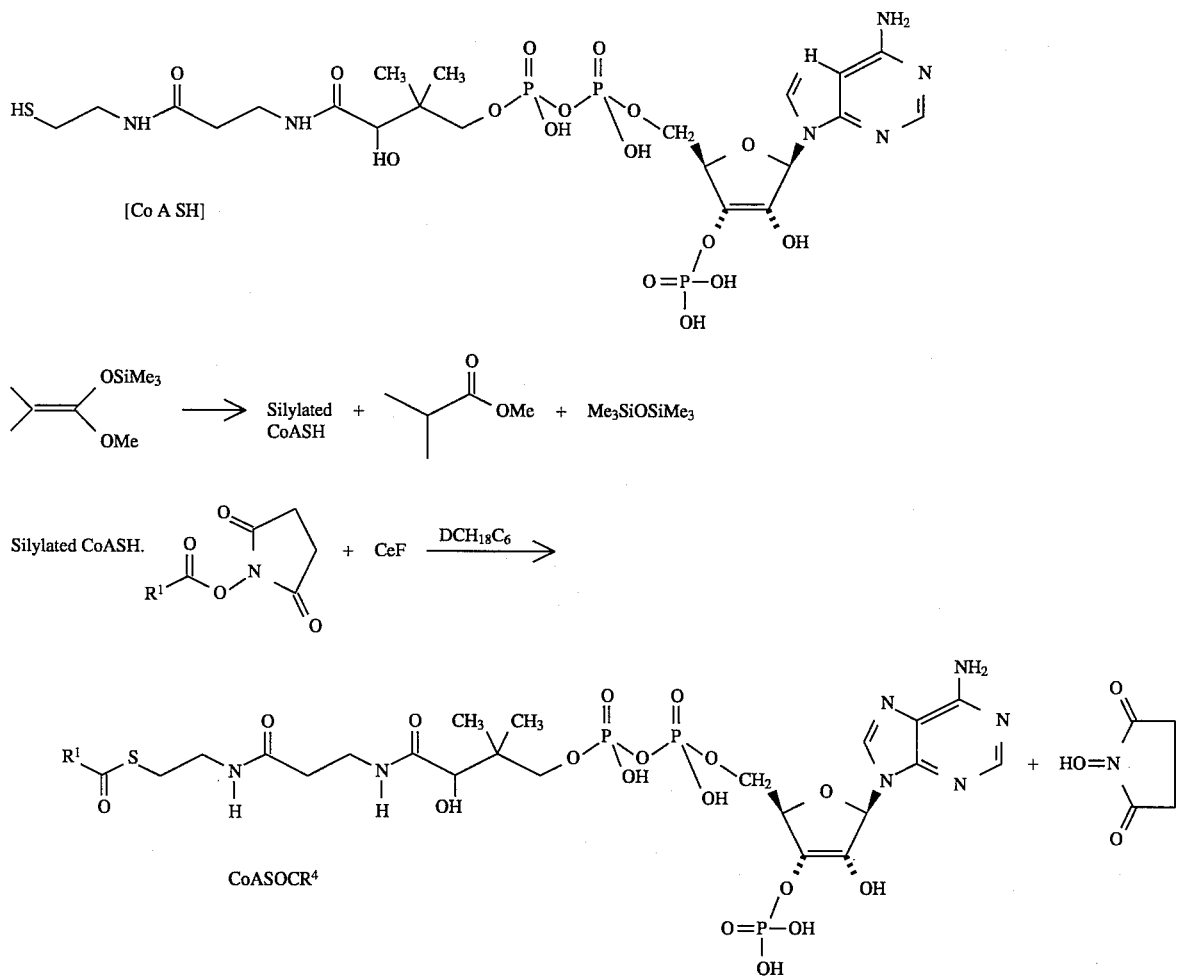

Ex. 1: $R^1 = CH_3(CH_2)_{18}$.
Ex. 2: $R^1 = CH_3(CH_2)_{18}$.

EXAMPLE 1

Preparation of Icosanoyl Coenzyme A

1) Silylation of coenzyme A.

30 µl (104.0 µmole) of 1-methoxy-2-methyl-1-trimethylsilyloxypropene (ALDRICH) are added to a 1 ml vial flask for 1 night and is then filtered to eliminate the dicyclohexyl urea formed and it is subject to a vacuum concentration. The product is then purified by silica gel chromatography using for the elution an ether/petroleum ether (50:50) mixture, followed by recrystallization in ethanol and the obtaining of a white powder (yield 95%).

The characteristics of this product are as follows:
— mass spectrometry: (DCI/NH$_3$)M+18=427
— elementary analysis: (in %)
— calculated: C 70.37, H 10.58, O 16.6, N 3.42
— found: C 70.09, H 10.3, O 15.75, N 3.31
— IR (cm$^{-1}$): 2990 (vC—H), 1820, 1740 (vC=O), 1450, (δCH2), 1375 (δCH3), 1200(vC—O), 1060
— RMN$^1$H(CDCl$_3$ 300 MHz): δ0.86 (t, J=6.3 Hz, 3H, CH$_3$), δ1.24 (28H, CH$_2$), δ1.78 (tt, 2H, CH$_2$—CH$_2$—CO$_2$N), δ2.58 (t, J=6.2 Hz, 2H, CH$_2$—CH$_2$—CO$_2$N)δ2.82 (s, 4H, N—CO—CH$_2$—CH$_2$—CO—N).
— RMN$^{13}$C (CDCl$_3$ 75 MHz): δ168.41 (O—C=O), δ168.86 #(N—C=O).

b) Condensation of the coenzyme A with the N-hydroxysuccinimide ester.

To a 25 ml round-bottomed flask containing 50 mg (25 equiv) of cesium fluoride. 15 mg (10 mole % based on the cesium fluoride) of dicyclohexyl-18-C-6 and 7.5 mg (1.5 equiv) of icosanoic acid ester and N-hydroxysuccinimide obtained previously, are added 13 μmole of silylated coenzyme A obtained in a first stage dissolved in 1 ml of freshly distilled THF. The reaction medium is maintained under nitrogen for 6 h at 0° C. and then the reaction is stopped by adding 10 mM KH$_2$PO$_4$, filtration takes place on an ANOTOP 10$^+$filter (0.2 μm) and the product obtained is analyzed by analytical high performance liquid chromatography (HPLC).

For the analytical chromatography use is made of a NUCLEOSIL C-18 5 μm (250×4.6 mm, INTERCHIM), analytical column under the following conditions:
— AU=0.01
— $\lambda$max=254 nm
— elution rate=1.5 ml/min
— eluent: mixture of A (10 mM KH$_2$PO$_4$) and B (CH$_3$CN) with a linear gradient under the following conditions: within 10 min 60% A–40% B are passed to 55% A–45% B and then in 10 min to 45% A–55% B, in 15 min to 15%A–85% B and 10 min to 60% A–40% B.

For semipreparative chromatography use is made of a C 18 5 μm (250×10 mm, INTERCHIM) NUCLEOSIL column under the following conditions:
— AU=0.1
— $\lambda$max=254 nm,
— elution rate=1.5 ml/min
— eluent: mixture of A (10 mM KH$_2$PO$_4$) and B (CH$_3$CN) with a linear gradient
under the following conditions: in 10 min one passes from 60% A–40% B to 55% A–45% B, then in 10 min to 45% A–55% B, in 15 min to 20% A–20% B and in 10 min to 60% A–40% B.

The retention times of the different products characterized are 1 min for CoASH, 1.2 min for the dimer (CoAS)$_2$ and 23 min for icosanoyl-CoA.

The acetonitrile is evaporated under reduced pressure and the remaining aqueous phase is iyophilized. The product then undergoes salt removal on the same column after it has been rinsed with water. The residue is deposited on the column, washed with water for 40 min at an elution rate of 1.5 ml/min and then eluted with methanol at the same rate. The solvent is then concentrated and the product obtained is resolubilized in water, then lyophilized and kept at −18° C.

The characteristics of the product obtained are given in the following Table 1.

EXAMPLE 2

Preparation of the Octadecanoyl-coenzyme A

The same operating procedure as in example 1 is followed for preparing this acylated derivative, except that the ester of N-hydroxysuccinimide is prepared by using octadecanoic acid in place of icosanoic acid.

The characteristics of the product obtained are given in the following Table 1.

TABLE 1

|  | Ex. 1 = icosanoyl coenzyme A | Ex. 2 = octadecanoyl coenzyme A |
|---|---|---|
| Yield: % | 78 | 78 |
| NMR $^1$H (300 MHz) | NMR $^1$H(CDCl$_3$ 300 MHz): δ0.86(t, J=6.3Hz, 3H, CH$_3$, δ1.24(28H, CH$_2$), δ1.55(v, 2H, CH$_2$—CH$_2$—CO$_2$S), δ2.9(t, J=6.2Hz, 2H, CH$_2$—CH$_2$—CO$_2$S) | |
| UV: nm | $\epsilon$257 nm = 7809<br>$\epsilon$197 nm = 10236 | $\epsilon$257 nm = 12509<br>$\epsilon$197 nm = 25835 |
| FAB: m/z | 1063 | |
| Rf: min | 23 | 18 |

EXAMPLE 3

Preparation of the Icosanoyl-coenzyme A

This example follows the same operating procedure as in example 1 for preparing the silylated derivative of coenzyme A and the condensation and deprotection stage is then performed in the following way using as the activated acid the ester of icosanoic acid and N-hydroxysuccinimide prepared in the same way as in example 1.

To a 25 ml round-bottomed flask containing 50 mg of cesium fluoride (25 equiv), 15 mg (10 mole %) of DCH-18-C-6, 7.5 mg (1.5 equiv) of N-hydroxysuccinimide-activated acid, is added 1 equiv of the silylated coenzyme A dissolved in 1 ml of THF/CH$_3$CN (2:1). The reaction medium is maintained under nitrogen for 6 h at 25° C. The reaction is then stopped by adding 10 mM-KH$_2$PO$_4$ and then the product obtained is separated, purified and analyzed under the same conditions as in example 1. The reaction yield is 75%.

EXAMPLES 4 TO 6

Preparation of Icosanoyl-coenzyme A

These examples follow the same operating procedure as in example 3, except with respect to the activated acid quantity used for varying the activated acid/coenzyme A ratio from 2:1 to 1:2.

The ratios used and the yields obtained under these conditions are given in Table 2.

TABLE 2

| EX. | ACTIVATED ACID/COENZYME A MOLAR RATIO | YIELD (%) (+5%) |
|---|---|---|
| 3 | 1.5/1 | 75 |
| 4 | 2/1 | 75 |
| 5 | 1/1 | 69 |
| 6 | 1/2 | 60 |

EXAMPLES 7 TO 18

Preparation of Icosanoyl-coenzyme A

These examples follow the same operating procedure as in example 3 for preparing said acylated derivative of coenzyme A, but use is made of different organic solvents in the second condensation stage.

The solvents used and the yields obtained are given in Table 3.

TABLE 3

| EX. | SOLVENTS | YIELD (%) (+5%) |
|---|---|---|
| 7 | THF | 78.5 |
| 8 | CH$_3$CN | 72 |
|  | CH$_3$CN/THF |  |
| 9 | 2/1 | 65 |
| 10 | 1/1 | 75 |
| 11 | 1/2 | 75 |
| 12 | DME | 70 |
| 13 | CH$_2$Cl2 | 30 |
| 14 | AcOEt | 50 |
| 15 | Et$_2$O | 65 |
| 16 | acetone | 50 |
| 17 | EtOH | 30 |
| 18 | hexane | 10 |

EXAMPLE 19

Preparation of Icosanoyl-coenzyme A

This example follows the same operating procedure as in example 1 for preparing this acylated derivative, except with respect to the second stage which is performed under the following conditions.

1 equiv of the silylated derivative obtained in the first stage of example 1 is dissolved in 1 ml of anhydrous THF, to which are added 130 μl of tetrabutyl ammonium fluoride (8 equiv) which is left under stirring and nitrogen for 5 min at 25° C. 1.5 equiv of N-hydroxysuccinimide ester of icosanoic acid dissolved in 1 ml of anhydrous THF is added. After stirring for 1 h at ambient temperature, the product obtained is separated, analyzed and dosed by high performance liquid chromatography under the conditions described in example 1. The yield obtained is 55%.

EXAMPLES 20 TO 25

Preparation of Icosanoyl-coenzyme A

These examples follow the same operating procedure as in example 19, except that other organic solvents are used.

The results obtained and the solvents used are given in Table 4.

TABLE 4

| EX. | SOLVENTS | YIELD (%) (+5%) |
|---|---|---|
| 19 | THF | 55 |
| 20 | CH$_3$CN | 30 |
| 21 | DME | 10 |
| 22 | CH$_2$Cl$_2$ | 0 |
| 23 | AcOEt | 0 |
| 24 | Et$_2$O | 40 |
| 25 | acetone | 60 |

EXAMPLE 26

Preparation of Icosanoyl-coenzyme A

This example follows the same operating procedure as in example 1, except that the second condensation stage is performed under the following conditions.

To a 25 ml round-bottomed flask containing 50 equiv of potassium fluoride, 10 mole % (based on the potassium fluoride) of DCH-18-C-6 and 1.5 equiv of N-hydroxysuccinimide ester is added 1 equiv of silylated coenzyme A dissolved in 1 ml of THF/CH$_3$CN (2:1) mixture. The reaction medium is maintained under nitrogen for 3 h at 25° C. The product obtained is then separated and analyzed by HPLC. The reaction yield is 35/40%.

EXAMPLES 27 TO 34

Preparation of Icosanoyl-coenzyme A

These examples follow the same operating procedure as in example 26, except that different deprotection reagents are used and possibly different reagent quantities reaction temperatures and durations.

In examples 31 and 32 the deprotection reagent used is cesium fluoride alone without a crown ether-based catalyst, but the reaction mixture undergoes a sonication.

The reagents used, their quantity, the duration and temperature of the reaction, as well as the yields obtained are given in Table 5.

TABLE 5

| EX. | CATALYST | TIME (h) | T (°C.) | Yield (%) (+5%) |
|---|---|---|---|---|
| 26 | KF/dicyclohexyl-18-C-6 50 eq/10 mole % | 3 | 25 | 35/40 |
| 27 | CsF/dicyclohexyl-18-C-6 50 eq/2 mole % | 3 | 25 | 70 |
| 28 | CsF/dicyclohexyl-18-C-6 50 eq/10 mole % | 3 | 25 | 78 |
| 29 | CsF/dicyclohexyl-18-C-6 25 eq/10 mole % | 3 | 25 | 78 |
| 30 | CsF 25 eq | 3 | 25 | 62 |
| 31 | CsF/sonication 25 eq | 3 | 25 | 60 |
| 32 | CsF/sonication 25 eq | 1½ | 0 | 75 |
| 33 | AlCl$_3$ |  |  | 5 |
| 34 | [φ$_3$SnF$_2$]—[NBu$_4$]$^+$ |  |  | 0 |

On the basis of the results of Table 5, it is clear that the best results are obtained when using cesium fluoride as the deprotection reagent, either with a crown ether, or by subjecting the mixture to a sonication.

EXAMPLES 35 TO 42

Preparation of the Icosanoyl-coenzyme A

These examples follow the same operating procedure as in example 3, but for performing the second condensation stage different reaction times and temperatures are used.

The reaction times, temperatures and the yields obtained are given in Table 6.

TABLE 6

| EX. | TEMPERATURE (°C.) | REACTION TIME (h) | YIELD (%) (+5%) |
|---|---|---|---|
| 35 | −10 | 6 | <30 |
| 36 | 0 | 6 | 78 |
| 37 | 25 | 3 | 72 |
| 38 | 40 | 1½ | 60 |
| 39 | 60 | <½ | <30 |
| 40 | 25 | 1½ | 40 |
| 41 | 25 | 4½ | 75 |
| 42 | 25 | 24 | 70 |

EXAMPLE 43

Preparation of the Icosanoyl-coenzyme A

This example follows the same operating procedure as in example 3 for preparing the silylated derivative of coenzyme A and the second stage is carried out using in place of the N-hydroxysuceinimide ester, the icosanoic acid activated by isobutyl chloroformate. In order to prepare said activated acid, the following procedure is used.

26.0 μmole (3.8 μl) of anhydrous triethylamine are added to 26.0 μmole of icosanoic acid dissolved in 0.5 ml of anhydrous dichloromethane, under argon.

After stirring for 10 min to the reaction mixture are added 26.0 μmole (3.5 μl) of isobutyl chloroformate (ALDRICH) at 0° C. and the reaction mixture is left at ambient temperature for 2 h. Thus, a white suspension is obtained, which is filtered under nitrogen and concentrated under reduced pressure to obtain a white solid.

The condensation of this activated acid is then performed on coenzyme A working under the same conditions as in example 3, i.e. using 50 equiv of cesium fluoride in the presence of DCH-18-C-6 (10 mole %), an activated acid/coenzyme A molar ratio of 1.5:1 and a reaction time of 6 h at 25° C. The yield obtained is 50%.

EXAMPLE 44

This example follows the same operating procedure as in example 43, except that the activated acid used is that activated by 2,4,6-trichlorobenzoyl chloride and in which said activated acid is prepared in the following way.

To 19.0 μmole of icosanoic acid dissolved in 2 ml of anhydrous THF are added 19.5 μmole (27 μl) of anhydrous triethylamine, under argon. The reaction medium is cooled in an ice bath and to it is added dropwise at 0° C. 19.5 μmole (30.0 μl) of 2,4,6-trichlorobenzoyl chloride. The reaction medium is maintained at ambient temperature for 2 h and this gives a white suspension, which is filtered under nitrogen and concentrated under reduced pressure in order to obtain the activated acid in the form of a white solid.

The following condensation stage is performed under the same conditions as in example 43. This gives a yield of 65% for the icosanoyl-coenzyme A.

The following examples demonstrate that it is possible to obtain acyl-coenzymes A with good yields, more particularly when using as the activated acid a N-hydroxysuccinimide ester and when the second condensation stage is performed in an organic solvent such as THF, the mixture of acetonitrile and THF (1:2) and dimethyl ether and using cesium fluoride as the deprotection reagent, either at 0° C. for 90 min with sonication or at 25° C. for 3 to 5 h in the presence of DCH-18-C-6.

Although in these examples saturated acids have been used, the invention also applies to the use of unsaturated activated acids e.g. having 1 to 6 double bonds.

EXAMPLE 45

Preparation of Octadecanoyl-enzyme A

The same operating procedure as in example 2 is followed for preparing this acylated derivative of coenzyme A, except that the reaction is performed for 5 hours. The acylation reagent, the reaction conditions, the product obtained and the yield obtained under these conditions are given in Table 7.

EXAMPLE 46

Preparation of the Octadecanoyl-coenzyme A

The same operating procedure as in example 45 is used, except that the acylation reagent used is the ester of octadecanoic acid and N-hydroxyphthal imide and the reaction is performed using as the deprotection reagent rubidium fluoride in place of cesium fluoride.

The acylation reagent, the reaction conditions, the derivative obtained and the isolated product yield are given in Table 7. This table shows that the replacement of cesium fluoride by rubidium fluoride and the use of the N-hydroxyphthalimide ester leads to an improved product yield.

EXAMPLE 47

Preparation of the Icosanoyl-coenzyme A

This example follows the same operating procedure as in example 1 for preparing this acylated derivative, but the reaction is performed for 5 hours. The acylation reagent, the reaction conditions and the result obtained are given in Table 7.

EXAMPLE 48

Preparation of the Icosanoyl-coenzyme A

This example follows the same operating procedure as in example 47, but the catalyst used is amine TDA-1 instead of crown ether. The acylation reagent, the reaction conditions and the results obtained are given in Table 7.

EXAMPLE 49

Preparation of the Icosanoyl-coenzyme A

This example follows the same operating procedure as in example 47, but rubidium fluoride is used in place of cesium fluoride. The acylation reagent, the reaction conditions and the result obtained are given in Table 7.

EXAMPLE 50

Preparation of the Icosanoyl-coenzyme A

This example follows the operating procedure of example 49, but the acylation reagent is constituted by the ester of N-hydroxyphthalimide and the catalyst is constituted by an amine, TDA-1. The acylation reagent, the reaction conditions and the result obtained are given in Table 7.

On comparing the results obtained in examples 47 to 50, it can be seen that the product yields are the same, no matter what the deprotection reagent, the catalyst and the acylation reagent used.

EXAMPLE 51

Preparation of 2-fluoro-2-icosanoyl-coenzyme A

This example follows the same operating procedure as in example 45 for preparing said compound using as the acylation reagent the ester of 2-fluoro-2-icosenoic acid and N-hydroxysuccinimide. The acylation reagent, the reaction conditions and the result obtained are given in Table 7.

EXAMPLE 52

Preparation of 2,fluoro-2-icosenoyl-coenzyme A

This example follows the operating procedure of example 51, but the acylation reagent used is the ester of 2-fluoro-2-icosanoic acid and N-hydroxyphthal imide and the deprotection agent used is rubidium fluoride in place of cesium fluoride. The acylation reagent, the reaction conditions and the result obtained are given in Table 7.

A comparison of the results of examples 51 and 52 shows that the use of the ester of N-hydroxyphthalimide and rubidium fluoride makes it possible to obtain an improved yield.

EXAMPLE 53

Preparation of 4-fluoro-3-hydroxy-icosanoyl-coenzyme A

This example follows the same operating procedure as in example 45 using as the acylation reagent the ester of 4-fluoro-3-hydroxyicosanoic acid and N-hydroxysuccinimide. The acylation reagent, the reaction conditions and the result obtained are given in Table 7.

TABLE 7

| Example | Acylation Reagent | $R_1$ | Reaction Conditions | Acyl-CoA | Yiueld of Product isolated by HPLC |
|---|---|---|---|---|---|
| 45 | $R^1$-C(O)-O-N(succinimide) | $C_{17}H_{35}$ | THF CsF/DCH-18-C-6 5 h | $C_{17}H_{35}$-C(O)-SCoA | 60% |
| 46 | $R^1$-C(O)-O-N(phthalimide) | $C_{17}H_{35}$ | THF RbF/DCH-18-C-6 5 h | $C_{17}H_{35}$-C(O)-SCoA | 85% |
| 47 | $R^1$-C(O)-O-N(succinimide) | $C_{19}H_{39}$ | THF CsF/DCH-18-C-6 5 h | $C_{17}H_{35}$-CH$_2$-C(O)-SCoA | 80% |
| 48 | $R^1$-C(O)-O-N(succinimide) | $C_{19}H_{39}$ | THF CsF/TDA-1 5 h | $C_{17}H_{35}$-CH$_2$-C(O)-SCoA | 80% |
| 49 | $R^1$-C(O)-O-N(succinimide) | $C_{19}H_{39}$ | THF RbF/DCH-18-C-6 5 h | $C_{17}H_{35}$-CH$_2$-C(O)-SCoA | 80% |
| 50 | $R^1$-C(O)-O-N(phthalimide) | $C_{19}H_{39}$ | THF RbF/TDA-1 5 h | $C_{17}H_{35}$-CH$_2$-C(O)-SCoA | 80% |
| 51 | $R^1$-C(O)-O-N(succinimide) | $C_{17}H_{35}$-CH=CF- | THF CsF/DCH-18-C-6 5 h | $C_{17}H_{35}$-CH=CF-C(O)-SCoA | 60% |

TABLE 7-continued

| Example | Acylation Reagent | $R_1$ | Reaction Conditions | Acyl-CoA | Yiueld of Product isolated by HPLC |
|---|---|---|---|---|---|
| 52 | (phthalimide-N-O-C(O)-R¹) | $C_{17}H_{35}$–CH=CF– | THF RbF/DCH-18-C-6 5 h | $C_{17}H_{35}$–CH=CF–C(O)SCoA | 70% |
| 53 | (succinimide-N-O-C(O)-R¹) | $C_{16}H_{33}$–CHF–CH(OH)–CH₂– | THF CsF/DCH-18-C-6 5 h | $C_{16}H_{33}$–CHF–CH(OH)–CH₂–C(O)SCoA | 80% |

THF: Tetrahydrofuran
DCH-18-C-6: dicyclohexyl-18-C-6
TDA-1: $N(CH_2CH_2OCH_2CH_2OCH_3)_3$

We claim:

1. Silylated or stannylated coenzyme A prepared by the reaction of coenzyme A with a sylilation or stannylation reagent to at least partly replace the unstable hydrogens of the coenzyme A by a group of formula $SiR_3$ or $SnR_3$ in which the R's, which can be the same or different, are alkyl or aryl groups.

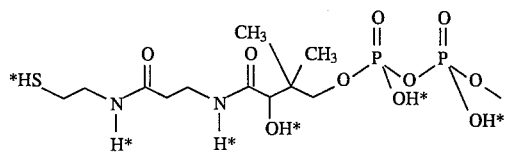

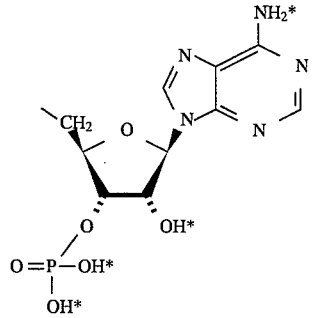

2. Silylated coenzyme A according to claim 1, characterized in that the R's of the group of formula $SiR_3$ represent a $C_1$ to $C_4$ alkyl group.

3. Acyl-coenzymes A in which the acyl group is the 4-fluoro-3-hydroxyicosanoyl or the 2-fluoro-2-icosenoyl group.

* * * * *